(12) United States Patent
Niazi (10) Patent No.: US 9,550,971 B2
(45) Date of Patent: Jan. 24, 2017

(54) UNIVERSAL BIOREACTORS AND METHODS OF USE

(75) Inventor: Sarfaraz K. Niazi, Deerfield, IL (US)

(73) Assignee: Therapeutic Proteins International, LLC, Chicago, IL (US)

( * ) Notice: Subject to any disclaimer, the term of this patent is extended or adjusted under 35 U.S.C. 154(b) by 1492 days.

(21) Appl. No.: 12/423,587

(22) Filed: Apr. 14, 2009

(65) Prior Publication Data

US 2010/0261226 A1  Oct. 14, 2010

(51) Int. Cl.
*C12N 1/20* (2006.01)
*C12M 1/00* (2006.01)

(52) U.S. Cl.
CPC ............. *C12M 29/04* (2013.01); *C12M 23/26* (2013.01); *C12M 23/58* (2013.01)

(58) Field of Classification Search
CPC ................................ C12M 23/58; C12M 23/26
See application file for complete search history.

(56) References Cited

U.S. PATENT DOCUMENTS

| | | | | |
|---|---|---|---|---|
| 3,946,780 | A * | 3/1976 | Sellers | B65D 51/1616 383/102 |
| 4,900,669 | A * | 2/1990 | Hatch | C12N 9/93 435/108 |
| 5,266,487 | A * | 11/1993 | Hatfield | 435/294.1 |
| 5,565,105 | A | 10/1996 | Thakor | |
| 5,688,687 | A | 11/1997 | Palsson et al. | |
| 6,048,721 | A | 4/2000 | Armstrong et al. | |
| 6,432,698 | B1 | 8/2002 | Gaugler et al. | |
| 6,544,788 | B2 | 4/2003 | Singh | |
| 6,673,598 | B1 | 1/2004 | Akers et al. | |
| 6,861,248 | B2 * | 3/2005 | Dale et al. | 435/255.2 |
| 7,144,727 | B2 | 12/2006 | Akers et al. | |
| 7,377,686 | B2 | 5/2008 | Hubbard | |
| 7,384,783 | B2 | 6/2008 | Kunas et al. | |
| 2005/0239198 | A1 | 10/2005 | Kunas et al. | |
| 2006/0270036 | A1 * | 11/2006 | Goodwin et al. | 435/395 |

(Continued)

FOREIGN PATENT DOCUMENTS

| | | |
|---|---|---|
| DE | 19953137 A1 | 5/2001 |
| DE | 10024494 A1 | 5/2002 |

(Continued)

OTHER PUBLICATIONS

Fenge et al., "Agitation, aeration and perfusion modules for cell culture bioreactors," *Cytotechnology* 11, pp. 233-244 (1993).

(Continued)

*Primary Examiner* — Jonathan Hurst
(74) *Attorney, Agent, or Firm* — Therapeutic Proteins International, LLC; Sarfaraz K. Niazi; Cheryl Liljestrand (57) ABSTRACT

Bioreactors suitable for housing a predetermined volume of culture medium comprising a plurality of containers of approximately equal internal volume in which the culture medium resides, wherein the predetermined volume of culture medium is retained in approximately equal amounts within each of the plurality of containers during operation of the bioreactor, and wherein the internal volume of each container is selected so that the amount of culture medium in each container exceeds 50 vol. % of the container internal volume during operation of the bioreactor, and related methods of use.

1 Claim, 7 Drawing Sheets

(56) References Cited

U.S. PATENT DOCUMENTS

| | | | |
|---|---|---|---|
| 2007/0269888 A1 | | 11/2007 | Houtzager et al. |
| 2008/0274494 A1* | | 11/2008 | Kertz .............................. 435/29 |
| 2008/0299643 A1* | | 12/2008 | Howard et al. ............ 435/252.1 |
| 2009/0035856 A1 | | 2/2009 | Galliher et al. |
| 2009/0280565 A1* | | 11/2009 | Jolicoeur et al. ............. 435/412 |

FOREIGN PATENT DOCUMENTS

| | | | |
|---|---|---|---|
| JP | 5 277304 A | 10/1993 | |
| JP | 5 317606 A | 12/1993 | |
| JP | 8 196994 A | 8/1996 | |
| JP | 7 68104 A | 10/2006 | |
| JP | 39 26041 B2 | 6/2007 | |
| JP | 39 29800 B2 | 6/2007 | |
| JP | 39 36996 B2 | 6/2007 | |
| WO | WO 2006/128641 * | 10/2006 | ............... C12M 1/04 |

OTHER PUBLICATIONS

Henzler et al., "Oxygenation of cell cultures," *Bioprocess Eng.* 9, pp. 61-75 (1993).

Krahe M., "Biochemical Engineering," Reprint from *Ullmann's Encyclopedia of Indus. Chem.*; VCH Publishers: Weinheim, Germany, vol. 6 (2003).

Nelson, K.L. et al., "Industrial scale mammalian cell culture, Part I: Bioreactor design considerations," *BioPharm.*, 1, pp. 42-46 (1988).

Nehring et al., "Experimental study of a ceramic microsparging aerations system in a pilot scale animal cell culture," *Biotechnol. Progress*, 20, pp. 1710-1717 (2004).

Marks, D.M., "Equipment design consideration for large scale cell culture," *Cytotechnology*, 42, pp. 21-33 (2003).

Chisti, Y. "Animal-cell damage in sparged bioreactors," *Trends Biotechnol*, 18, pp. 420-432 (2000).

Papoutsakis E.T. et al., "Fluid-mechanical damage of animal cells in bioreactors," *Tibtech*, 9, pp. 427-437 (1991).

Chalmers J.J. et al., "Cells and bubbles in sparged bioreactors," *Cytotechnology*, 15, pp. 311-320 (1994).

Kunas K.T. et al.," Damage mechanisms of suspended animal cells in agitated bioreactors with and without bubble entrainment," *Biotechnology and Bioengineering*, 36, pp. 476-483 (1990).

Nehring D., Czermak, P., "Ein neues Begasungssystem fur Zelkulturen im Labor- und ProduktionsmaBstab, in Bechmann, D. (Hrsg.); Technische System fur Biotechnologie und U"mwelt—Biosensorik und Zelkulturtechnik, S. 265-272, ISBN 3-503-06645-4, Erich Schmidt Verlag, Berlin (2002).

Zhang S. et al., "A comparison of oxygen methods for high-density perfusion cultures of animal cells," *Biotechnology and Bioengineering*, 41, pp. 685-692 (1993).

Martens, D.; Tramper, J. "Lethal events during gas sparging animal cell culture," *Biotechnology and Bioengineering*, 37, pp. 484-490 (1991).

Michaels, J.D. et al., "Sparging and agitation-induced injury of cultured animal cells: do cell-to-bubble interactions in the bulk liquid injure cells?" *Biotechnology and Bioengineering*, 51, pp. 399-409 (1996).

Meier S.J.; Hatton, T. A.; Wang, D.I.C. "Cell death from bursting bubbles; role of cell attachment to rising bubbles in sparged reactors," *Biotechnology and Bioengineering*, 62, pp. 468-478 (1999).

"Appendix A: Technical Reference," Wave Bioreactors (Aug. 2006).

Charles et al., "Single-Use Technologies—A Contract Biomanufacturer's Perspective," *BioPharm International Guide*, Nov. 2007.

Wave Mixer 2006 Catalog, Selection Guide (May 2006).

Wave Disposable Technology (Aug. 2008).

Pierce et al. "Scalability of Disposable Bioreactor from 25L-500L Run in Perfusion Mode with a CHO-Based Cell Line: A Tech Review," Reprinted from *BioProcessing Journal*, vol. 3, No. 4, Jul./Aug. 2004.

Hami et al., GMP production and testing of Xcellerated T Cells™ for the treatment of patients with CLL, *Cytotherapy*, vol. 6, No. 6, pp. 554-562 (2004).

Namdev et al., "Assessing a Disposable Bioreactor for Attachment-Dependent Cell Cultures," Reprinted from *BioPharm* (Feb. 2000).

Kranjac et al., Validation of Bioreactors: Disposable vs. Reusable, *BioProcess International*, Industry Yearbook (2004).

* cited by examiner

UNIVERSAL BIOREACTORS AND METHODS OF USE

BACKGROUND OF THE INVENTION

A variety of vessels and methods have been developed over the years to carry out chemical, biochemical and/or biological processing. Stainless steel fermentation vessels of several hundreds of thousands liters are not uncommon for the growth of microorganisms that produce enzymes or secondary metabolites. The methods include batch, fed-batch, continuous or semi-continuous perfusion. Gradually, more challenging cultures such as mammalian, insect or plant cells have been adapted for growth in fermentation vessels using highly specialized media. Although the design of these vessels differs in detail, they have several common features. The cells are kept in suspension by rotating stirring blades placed vertical in the vessel, and gas exchange is facilitated by injection of air, oxygen or carbon dioxide.

There are several drawbacks to this design: the shearing forces that are introduced through the stirring blades and the cavitation of miniscule air bubbles is detrimental to more sensitive cell types or organisms. Also, these vessels have to be rigorously cleaned between production runs to prevent cross-contamination, which is time consuming and needs to be validated for individual cultures. Furthermore, the use of stirred fermentors requires highly trained operators. The cost price for stirred fermentors is high across the whole size range and therefore they are used repeatedly over long periods of time, thus increasing infection risks as a result of mechanical failures. Perhaps most significantly, the optimization of culture conditions for stirred fermentors in a small scale cannot be transferred in a linear way to commercial scale production. For example, the fluid dynamics, aeration, foaming and cell growth properties change with an order of magnitude when the scale increases. In addition, for more delicate cell types or organisms, a large scale stirred fermentation vessel is not a viable device, even when more subtle stirring techniques such as airlift fermentors are used.

These drawbacks have led to the development of disposable fermentors. Examples of such disposable fermentors are systems based on wave agitation. See, e.g., U.S. Pat. No. 6,544,788; PCT Publication WO 00/66706. This type of fermentor may be used to culture relatively sensitive cells such as CHO cells (e.g., Pierce, *Bioprocessing J.* 3: 51-56 (2004)), hybridoma cells (e.g., Ling et al., *Biotech. Prog.*, 19: 158-162 (2003)), insect cells (e.g., Weber et al., *Cytotech.* 38: 77-85 (2002)) and anchorage-dependent cells (e.g., Singh, *Cytotech.* 30: 149-158 (1999)) in a single disposable container. Such disposable units are relatively cheap, decrease the risk of infection because of their single use and require no internal stirring parts as the rocking platform induces wave-like forms in the liquid phase to facilitate gas exchange. However, this principle cannot be expanded to the size of hundreds of thousands of liters (such as the industrial fermentors) but are currently available from 1 liter to 500 liters (total volume of the disposable bag, available from Wave Biotechnology AG, Switzerland; Wave Biotech Inc., USA). Moreover, the hydrodynamics for each size of these disposable bags will differ as a result of differences in depth and height. Therefore, the use of these disposable bags requires optimization and re-validation of each step in an up-scaling process.

Although bioreactor systems and related processes are known, improvements to such systems and processes would be useful in the preparation of a variety of products produced from a biological source.

BRIEF SUMMARY OF THE INVENTION

The invention provides in one aspect a bioreactor suitable for housing a predetermined volume of culture medium comprising a plurality of containers of approximately equal internal volume in which the culture medium resides, wherein the predetermined volume of culture medium is retained in approximately equal amounts within each of the plurality of containers during operation of the bioreactor, and wherein the internal volume of each container is selected so that the amount of culture medium in each container exceeds 50 vol. % of the container internal volume during operation of the bioreactor; the plurality of containers comprising a first container, a last container and, optionally, one or more containers intermediate the first and last containers, each container comprising at least one culture medium inlet, at least one culture medium outlet, at least one gas inlet, at least one sparging filter attached to the at least one gas inlet, the filter comprising a plurality of pores on at least a portion thereof, at least one of said plurality of pores extending into the culture medium, at least one gas exhaust, at least one foam trap attached to the at least one gas exhaust, at least one inlet in fluid communication with the foam trap, one or more sensors for sensing one or more parameters of the culture medium, a flow conduit which permits the flow of culture medium through the at least one culture medium outlet of a container and into a subsequent container through the at least one culture medium inlet thereof, wherein during operation of the bioreactor there is continuous movement of culture medium from one container to an adjacent container; the first container further comprising a culture medium recycle inlet; a recycle conduit which permits the flow of culture medium from the culture medium outlet of the last container and into the first container through the culture medium inlet thereof; a controllable pump to effect movement of the culture medium through the recycle conduit; a recycle valve for controlling the amount of culture medium which is recycled from the last container into the first container, wherein the amount of culture medium that is recycled varies between 5 vol. % and 100 vol. %, the volume percent being calculated on the basis of the amount of culture medium in the final container; and at least one selectively movable base which supports each container, wherein movement of the base induces movement of the culture medium within each container.

A related aspect of the invention provides a method for producing a biological product from a culture medium of a predetermined volume comprising (a) providing a bioreactor as described in the preceding paragraph; (b) filling each container with an amount of culture medium sufficient to fill at least 50 vol. % of the internal volume of the container; (c) activating the selectively movable base to impart motion to the culture medium; (d) activating the pump to recycle culture medium from the last container to the first container, the culture medium continuously flowing from the first container, to an intermediate container if present, and to the last container; (e) detecting the density of cells in the culture medium in a container at predetermined time intervals; and (f) removing the culture medium and the biological product produced thereby from the bioreactor when the density of the cells in the culture medium in the container reaches a predetermined value.

A further aspect of the invention provides a method of preparing a biological product in a bioreactor from a predetermined volume of culture medium comprising (a) determining the total amount of culture medium necessary to produce the desired amount of biological product; (b) selecting a plurality of containers of approximately equal internal volume, the plurality of containers comprising a first container, a last container and, optionally, one or more containers intermediate the first and last containers, wherein the quantity and internal volume of the containers allow the amount of culture medium in each container to exceed 50 vol. % of the container internal volume during operation of the bioreactor; wherein each container comprises at least one culture medium inlet, at least one culture medium outlet, at least one gas inlet, at least one sparging filter attached to the at least one gas inlet, the filter comprising a plurality of pores on at least a portion thereof, the portion of the filter comprising the pores extending into the culture medium, at least one gas exhaust, at least one foam trap attached to the at least one gas exhaust, at least one inlet in fluid communication with the foam trap, one or more sensors for sensing one or more parameters of the culture medium, the first container further comprising a culture medium recycle inlet; (c) assembling the bioreactor from the plurality of containers by (i) attaching a flow conduit to the at least one culture medium outlet of a container and into a container through the at least one culture medium inlet thereof to permit the flow of culture medium from the container into the subsequent container; (ii) attaching a recycle conduit which permits the flow of culture medium from the culture medium outlet of the last container and into the first container through the culture medium inlet thereof, (iii) incorporating a pump into the recycle conduit to permit movement of the culture medium through the recycle conduit; and (iv) incorporating a valve for controlling the amount of culture medium which is recycled from the last container into the first container; and (d) providing a base on which each container resides, wherein the base selectively imparts movement of the culture medium within each container during operation of the bioreactor; (e) filling each container with an amount of culture medium sufficient to fill at least 50 vol. % of the internal volume of the container; (f) activating the selectively movable base to impart motion to the culture medium; (g) activating the pump to recycle culture medium from the last container to the first container, the culture medium continuously flowing from the first container, to an intermediate container if present, and to the last container; (h) detecting the density of cells in the culture medium in a container at predetermined time intervals; and (i) removing the culture medium and the biological product produced thereby from the bioreactor when the density of the cells in the culture medium detected in the container reaches a predetermined value.

In another aspect, the invention provides a method for the preparation of a biological product from a culture medium comprising (a) providing a bioreactor system comprising (i) a plurality of containers for retaining the culture medium, the plurality of containers comprising a first container, a last container and a container intermediate the first and last containers, each container comprising at least one culture medium inlet, at least one culture medium outlet, at least one gas inlet, at least one sparging filter attached to the at least one gas inlet, the filter comprising a plurality of pores on at least a portion thereof, the portion of the filter comprising the pores extending into the culture medium, at least one gas exhaust, at least one foam trap attached to the at least one gas exhaust, at least one inlet in fluid communication with the foam trap, one or more sensors for sensing one or more parameters of the culture medium, (ii) a flow conduit comprising a valve which permits the flow of culture medium through the at least one culture medium outlet of a container and into a subsequent container through the at least one culture medium inlet thereof, (iii) at least one selectively movable base which supports each container, wherein movement of the base induces movement of the culture medium within each container, (b) charging the first container with culture medium comprising a component selected from the group consisting of mammalian cells, plant cells and bacteria, (c) moving the culture medium in the first container while introducing oxygen into the medium through the sparging filter until the desired density of the cells in the culture medium is obtained, (d) opening the valve in the flow conduit located between the first container and the intermediate container to permit the culture medium from the first container to enter the intermediate container, and closing the valve thereafter, (e) charging the first container with a culture medium comprising the component included in the culture medium of step (b), and adding culture medium to the cell culture medium present in the intermediate container, (f) moving the culture medium in each container while introducing oxygen into the medium through the sparging filter until the desired density of the cells in the culture medium in each container is obtained, (g) opening the valve in the flow conduit located between an intermediate container and the last container to permit the culture medium from the intermediate container to enter the last container, and closing the valve thereafter, (h) charging the first container with a culture medium comprising the component included in the culture medium of step (b), and adding culture medium to the culture medium present in each intermediate and last containers, (i) moving the culture medium in each container while introducing oxygen into each medium through the sparging filter until the desired density of the cells in the culture medium in each container is obtained, (j) removing the culture medium from the last container, opening the valve in the flow conduit located between an intermediate container and the last container to permit the culture medium from the intermediate container to enter the last container and closing the valve thereafter, and opening the valve in the flow conduit located between the first container and the subsequent intermediate container to permit the culture medium from the first container to enter the subsequent intermediate container and closing the valve thereafter, (k) charging the first container with a culture medium and, optionally, with the component included in the culture medium of step (b), and adding culture medium to the culture medium present in each of the intermediate and last containers, (l) moving the culture medium in each container while introducing oxygen into the culture medium through the sparging filter until the desired density of the cells in the culture medium in each container is obtained, and (m) repeating steps (j)-(l).

DETAILED DESCRIPTION OF THE INVENTION

In one aspect, the present invention provides a bioreactor suitable for preparing a biological product from a predetermined volume of culture medium, and a related method of use. More particularly, the invention provides an apparatus and method which is universal in the sense that the apparatus may be used to prepare a biological product regardless of the nature of the culture media.

Figure 4:
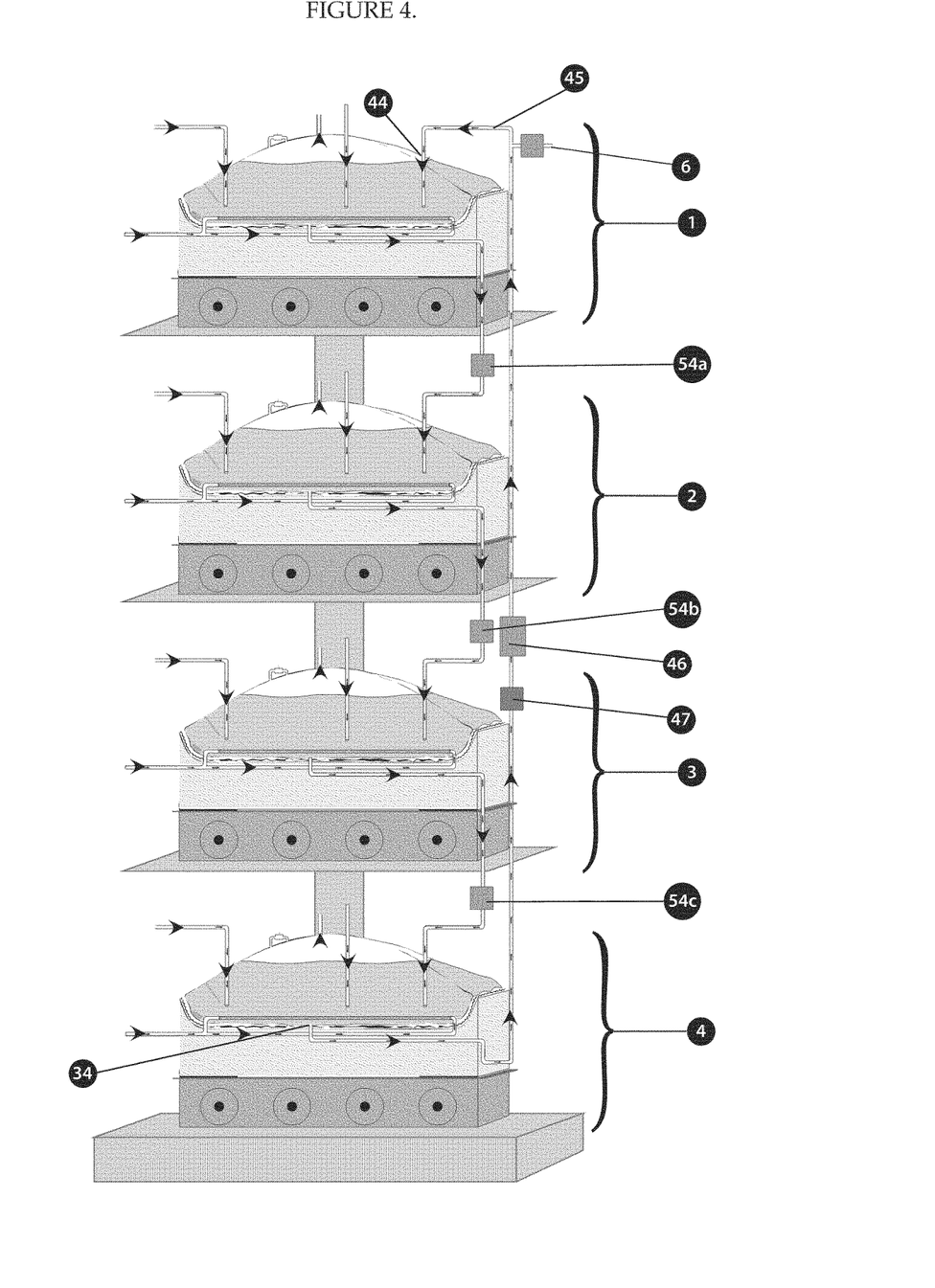
FIG. 4 is an illustration of four of the bioreactors depicted in FIG. 1 configured in accordance with another preferred embodiment of the invention.

Turning initially to FIG. 4, a side sectional view of a preferred embodiment of the inventive bioreactor is illustrated. In this embodiment, a plurality of containers of approximately equal internal volume are provided (1, 2, 3 and 4) in which the culture medium resides. As depicted in this figure, the predetermined volume of culture medium is retained in approximately equal amounts within each of the plurality of containers during operation of the bioreactor, and the internal volume of each container is selected so that the amount of culture medium in each container exceeds 50 vol. % of the container internal volume during operation of the bioreactor. In these embodiments, the plurality of containers used in the bioreactor comprise a first container 1, a last container 4 and, optionally, one or more containers (with two being provided in these illustrations) 2, 3 intermediate the first and last containers.

Figure 1:
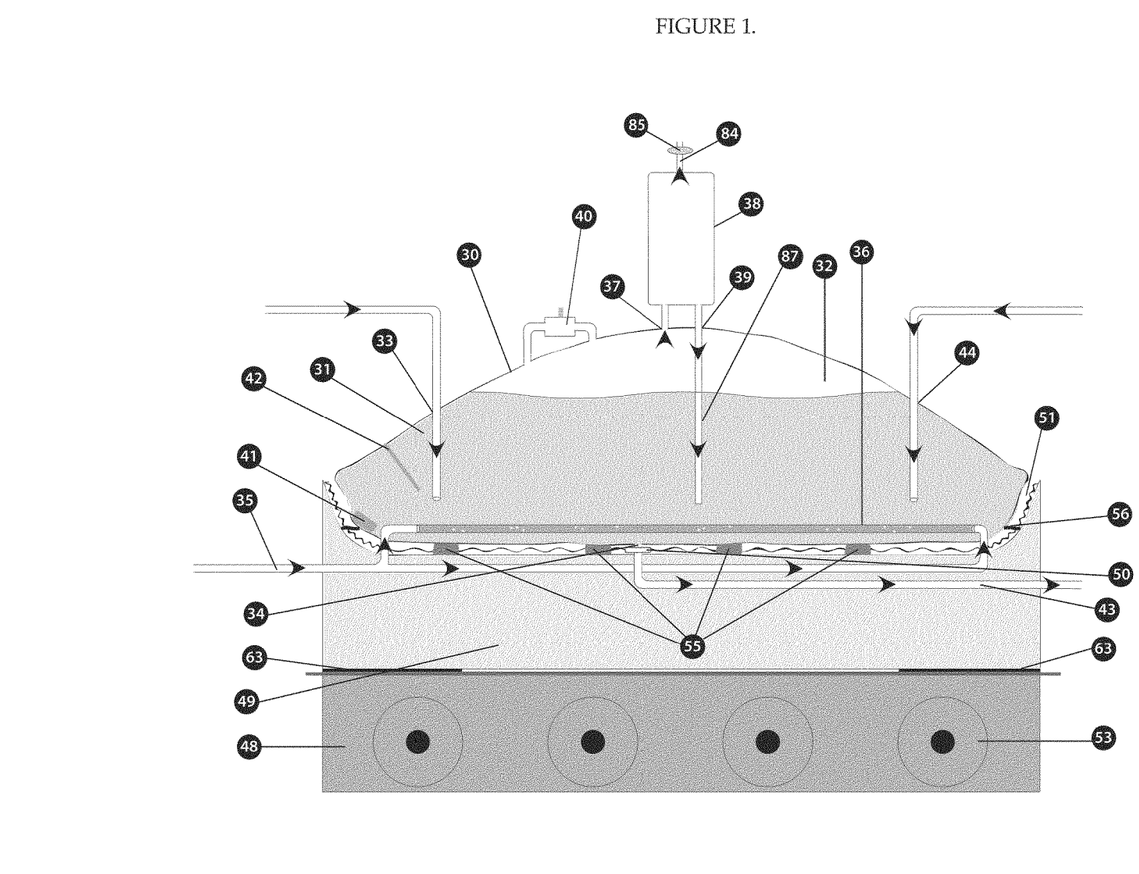
FIG. 1 is a side sectional view of a bioreactor in accordance with a preferred embodiment of the invention.

Turning to FIG. 1, there is illustrated a side sectional view of a preferred container 30, the interior of this container comprising culture medium 31 and a volume which is free of culture medium, the latter commonly referred to as headspace 32. The container, which alone may constitute a bioreactor, further comprises at least one culture medium inlet 33, at least one culture medium outlet 34, at least one gas inlet 35, at least one sparging filter 36 in fluid communication with the at least one gas inlet 35, the filter 36 comprising a plurality of pores on at least a portion thereof, at least one of said plurality of pores extending into the culture medium 31, at least one gas exhaust 37, at least one foam trap 38 in fluid communication with the at least one gas exhaust 37, at least one inlet 39 in fluid communication with the foam trap, and one or more sensors for sensing one or more parameters of the culture medium, e.g., pressure of the gas in the headspace 40, cell density, pH and/or carbon dioxide 41, and/or temperature 42.

Figure 2:
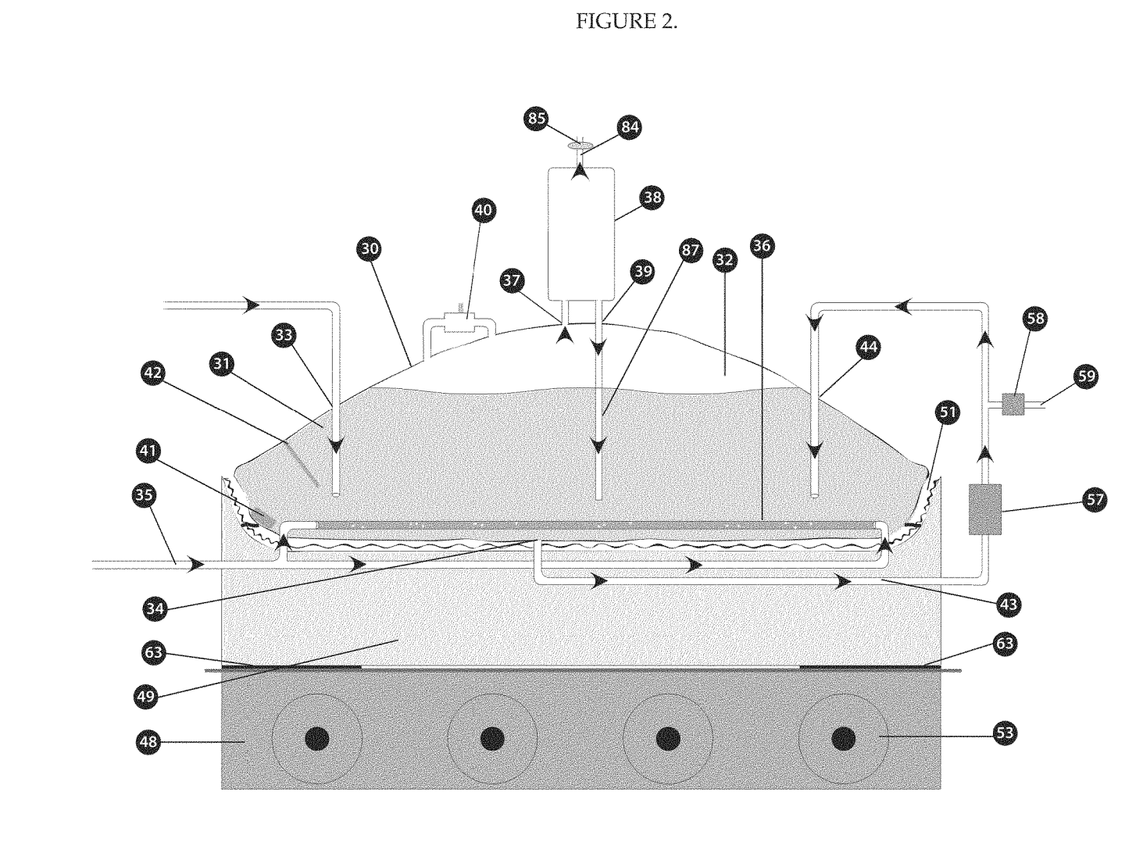
FIG. 2 is a side sectional view of the bioreactor depicted in FIG. 1 with certain additional components.

Turning to FIG. 2, there is illustrated a side sectional view of an embodiment of the bioreactor depicted in FIG. 1 which provides for sampling of the culture medium within a container. In this embodiment, the culture medium passes through the culture medium outlet 34, through a flow conduit 43 and into a pump 57, desirably a peristaltic pump, which provides for circulation of the culture medium within this sampling loop. A pinch valve 58 associated with a sampling outlet 59 allows a portion of the culture medium to be diverted for sampling, wherein the remainder of the culture medium is returned to the container via the culture medium return inlet 44.

Figure 5:
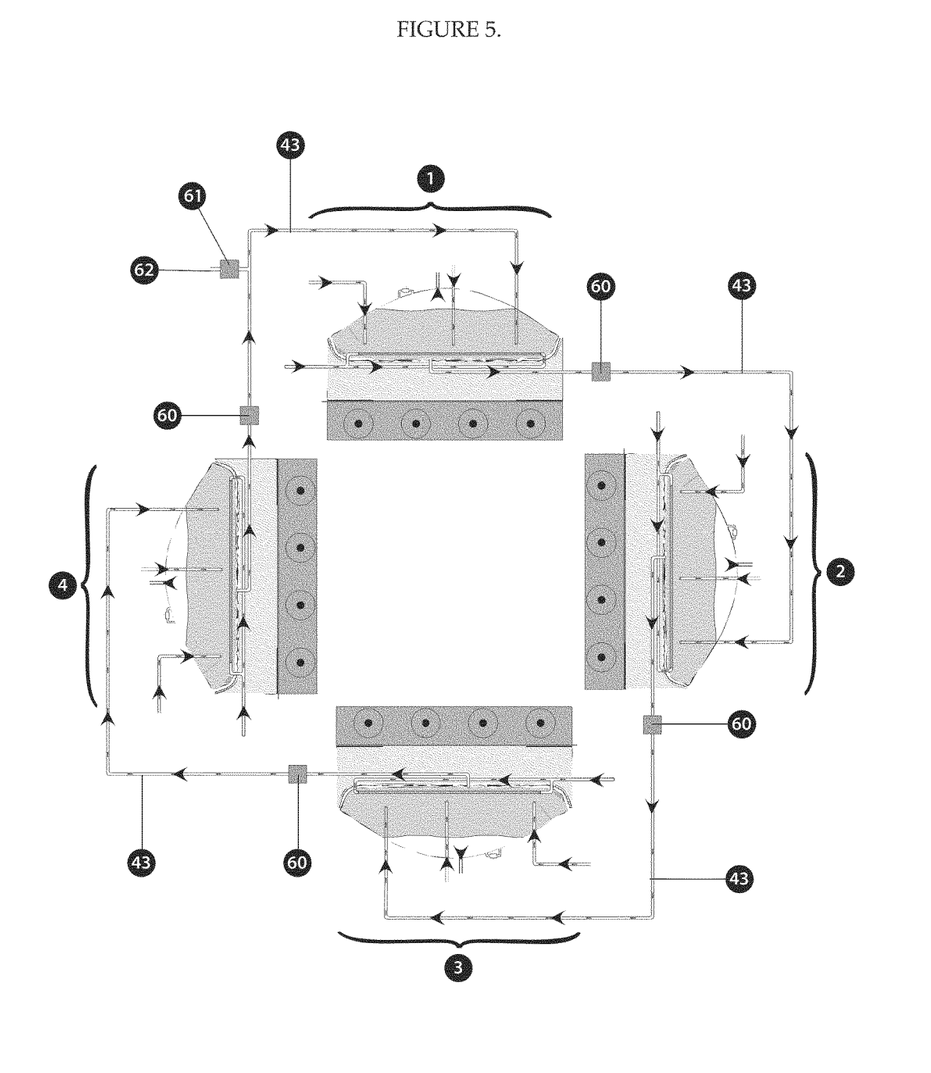
FIG. 5 is an illustration of four of the bioreactors depicted in FIG. 1 configured in accordance with another preferred embodiment of the invention.

In a preferred embodiment, the containers illustrated in FIG. 1 may be configured in series, as illustrated in FIGS. 4 and 5, to provide a bioreactor. During operation, the culture medium within this bioreactor is circulated within the plurality of containers. More specifically, a plurality of flow conduits 43 are provided which permit culture medium to pass through the at least one culture medium outlet of a container, through a flow conduit, and into a subsequent container through the at least one culture medium inlet thereof. This configuration permits the continuous movement of culture medium from a given container to an adjacent (downstream) container during operation of the bioreactor.

Turning to FIG. 4, the first container 1 comprises a culture medium return inlet 44. This inlet is in fluid communication with the culture medium outlet of the last container via a recycle conduit 45 (the culture medium outlet 34 of the last container not having a flow conduit 43 associated therewith). The recycle conduit 45 permits culture medium to flow from the last container into the first container. An illustration of an embodiment of this bioreactor comprising a plurality of containers (1, 2, 3, 4) and the recycle conduit 45 is provided in FIG. 4. As shown in FIG. 4, a controllable pump 46 also may be used to effect movement of the culture medium from the last container 4 through the recycle conduit 45 and into the first container 1. Also optionally provided is a controllable recycle valve 47 which may be used in conjunction with the controllable pump to vary the amount of culture medium which is recycled from the last container into the first container. During operation of the bioreactor, the culture medium is continuously cycled through the bioreactor, with the amount of culture medium that is recycled being variable, typically between 5 vol. % and 100 vol. %, more desirably between 40 vol. % and 100 vol. %, and even more desirably between 70 vol. % and 100 vol. %, and preferably between 80 vol. % and 100 vol. %, the volume percent being calculated on the basis of the amount of culture medium in the final container.

Turning to FIG. 5, a side sectional view of a related embodiment is depicted, wherein culture medium from a container is transferred into the subsequent container, e.g. from container 1 to container 2, from container 2 to container 3, from container 3 to container 4, and from container 4 to container 1. The flow conduits 43 which permit the flow of culture medium between containers include one or more controllable pumps 60 which induce the culture medium to flow between containers at a controllable rate (volume/minute). A pinch valve 61 associated with a sampling outlet 62 allows a portion of the culture medium to be diverted for sampling. The operation of the bioreactor may be halted, and subsequently drained, when the sampled culture medium reaches one or more predetermined conditions.

Turning to FIG. 1, each container in the bioreactor is supported by at least one selectively movable base 48, wherein the movement of the base induces movement of the culture medium within each container. The base is capable of one type of motion, and desirably a plurality of motions, the latter permitting an operator to select the type of motion desired in order to optimize the yield of the particular biological product being produced. One or more motors 53, desirably electric-powered, are used to impart motion to the base (and platform when present).

Desirably, and as illustrated in FIG. 1, the base may further comprise a raised platform 49 on which at least one container 30 may reside. This platform, which is commonly square or rectangular, but may be of any suitable shape, may include one or more sidewalls (vertical or, more preferably, vertically inclined) which assist in retaining the container on the base when the base is in motion. When a platform is provided, it is further desirable that the at least one culture medium outlet of a container 34 residing thereon be located on a portion of the container which is coextensive with the platform, wherein the platform includes an opening 50 therethrough which permits the culture medium to pass through the outlet of the container, into a flow conduit 43, and into the subsequent container (not shown). This raised platform provides a space through which the flow conduit may pass. If desired, more than one container may be provided on each base.

Advantageously, the base further includes a controllable heating element 51, desirably located between the upper surface of the platform and the lower portion of the container, but which may also be incorporated into the platform itself. This element, when activated, is able to increase the temperature of the culture medium with the container to a level which is optimal for the particular culture medium therein. The heating element may comprise a heat exchanger, a closed loop water jacket, an electric heating blanket, or a Peltier heater. Other heaters for heating a liquid inside a vessel are known to those of ordinary skill in the art and may be used alone or in combination with the foregoing device. The heater may also include a thermocouple and/or a resistance temperature detector (RTD) 42 for sensing a temperature of the contents inside the vessel. The thermocouple may be operatively connected to a process control module to control temperature of the contents in the vessel. Optionally, a heat-conducting material may be embedded in the surface of the container to provide a heat transfer surface to overcome the insulating effect of the material used to form other portions of the container.

Optionally, cooling of a container may be provided by a closed loop water jacket cooling system, a cooling system mounted on the base, or by standard heat exchange through a cover/jacket associated with the base, for example, a heat blanket or a packaged dual unit which provides heating and cooling may a component of a device configured for both heating/cooling but may also be separate from a cooling jacket. Cooling may also be provided by Peltier coolers.

The base may also include one or more selectively-operable sonicators to assist in the mixing of the culture medium during operation of the bioreactor. These sonicators 55, which emit ultrasonic waves, are desirably located on the bottom of the platform, with the platform including sidewalls, wherein the sonicator and the container are separated from one another by conducting gel 56, with the sonicator preferably being submerged in the gel. Activation of the sonicators may be continuous or intermittent, and may be optimized depending on the particular culture medium container in the bioreactor. When a plurality of sonicators is included, the sonicators may be activated simultaneously or independently of one another, depending again on the composition of the culture medium. The number of sonicators desirably varies in direct proportion to the container volume.

When sonicators are provided, it is desirable to pass the flow conduit 43 through a side wall of the base as opposed to the bottom of the base, this configuration minimizing leakage of any conducting gel residing therein.

Desirably, and as illustrated in FIG. 4, the containers 1, 2, 3, 4 are oriented in a vertical relationship, with the first container 1 located above any intermediate container 2, 3, and the last container 4 being located below the penultimate container in the apparatus. In this orientation, the flow of culture medium from the first container through any intermediate containers and into the last container is assisted by gravity, while also having the advantage of minimizing the use of floor space. FIG. 5 illustrates an alternative orientation, wherein the containers are positioned horizontally relative to each other.

Each of the flow conduits used in association with the bioreactors preferably comprise a tube or conduit which is more preferably flexible. These conduits may further, and more desirably, incorporate a controllable valve, preferably a pinch transducer 54a, 54b, 54c, as illustrated in FIG. 4. The operation of each valve may be governed by the absolute or relative amount of culture medium in each container, this being determined most desirably by one or more sensors, preferably a strain gauge (see 63 in FIG. 1) associated with each container which are positioned on the apparatus to detect the weight of each container. To the extent the weight of one or more containers varies from a predetermined value, a signal is sent from the sensor to a controller (not shown) which is capable of independently operating each such valve. The selective opening and/or closing of one or more valves would cause the flow of culture medium between containers to increase or decrease, with the weight of the containers ultimately reaching a desired predetermined value. Desirably, and when necessary, this controller will operate in concert with the controller (not shown) associated with the controllable recycle pump 46 to maintain the weight of the containers at a predetermined value. Alternatively, and more desirably, a single controller may be used to control the operation of the valves and the recycle pump.

As previously mentioned, the containers desirably include one or more sensors or probes for monitoring one or more process parameters inside the containers such as, for example, cell density, temperature, pressure, pH, dissolved oxygen (DO), dissolved carbon dioxide ($DCO_2$), mixing rate, and gas flow rate. The sensors for DO, pH and $DCO_2$ are desirably optical sensors, with the first two more desirably being disposable (e.g., TruFluor sensors, Finesse Solutions LLC, Santa Clara, Calif. or CellPhase sensors, Fluorometrix Corporation, Stow, Mass. 01775). Each sensor is intended to be in communication with a computer-implemented control system (e.g., a computer) for calculation and control of various parameters and for display and user interface. Such a control system may also include a combination of electronic, mechanical, and/or pneumatic systems to control the aforementioned processing parameters as required to stabilize or control the parameters (e.g., pH may be adjusted by the addition of $CO_2$ or ammonia). It should be appreciated that the control system may perform other functions and the invention is not limited to having any particular function or set of functions.

The one or more control systems described herein can be implemented in numerous ways, such as with dedicated hardware and/or firmware, using a processor that is programmed using microcode or software to perform the functions recited above or any suitable combination of the foregoing.

The processing device may also be in communication with various devices which can adjust the process parameters toward predetermined acceptable levels, for example, activating a heater, activating a gas inlet valve to adjust the oxygen or $CO_2$ levels, activating the gas outlet valve to reduce gas pressure in the headspace, and the like.

The inventive bioreactor may include plurality of intermediate containers. More particularly, the bioreactor may include three, four, five, six, seven or more intermediate containers, depending upon the desired quantity of finished product.

Figure 3:
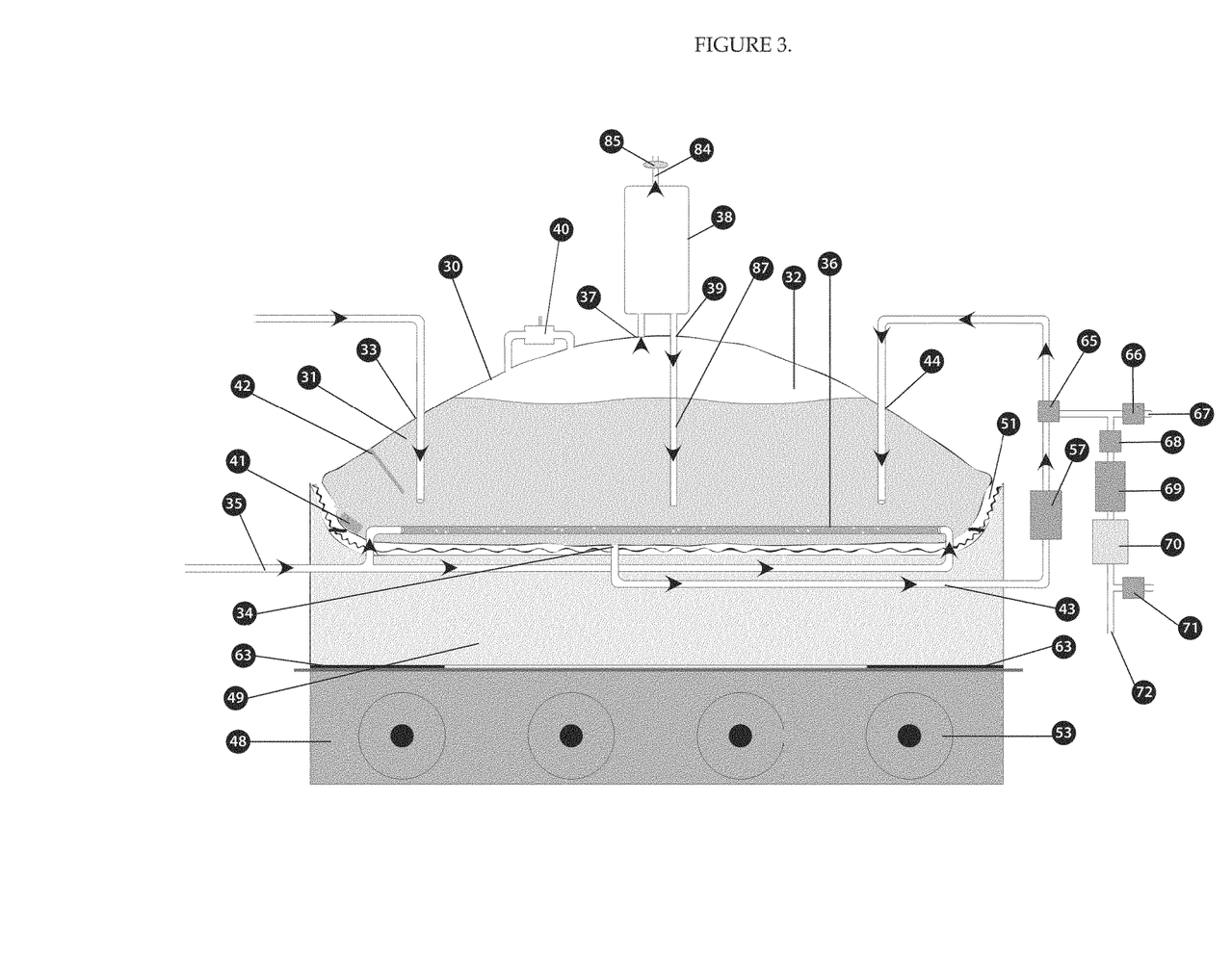
FIG. 3 is a side sectional view of the bioreactor depicted in FIG. 1 with certain additional components.

Optionally, it may be desirable to provide for perfusion. This may be most desirably provided by inclusion of a perfusion valve in the apparatus. Turning to FIG. 3, there is illustrated a bioreactor in accordance with FIG. 1 which incorporates a preferred perfusion system. In this embodiment, the flow conduit 43 permits culture medium to be removed through the culture medium outlet 34, with a controllable pump 64, preferably a peristaltic pump, providing for the flow of culture medium through the conduit. When desired, the culture medium, in any amount, may be diverted by way of a valve 65 to a side passage whereby the opening of a sample valve 66, preferably a pinch valve, permits a portion of all of the culture medium to pass into a sampling outlet 67, and whereby opening of a perfusion valve 68 permits the culture medium to be moved via a controllable pump 69, preferably a perfusion pump, into a filter 70 which separates the solids in the culture medium from the liquid. A subsequent valve 71, preferably a pinch valve, allows, if desired, the liquid may be transferred to a collection vessel 72

Upon operation, perfusion may be performed continuously or periodically. When perfusion is provided, additional fresh culture medium may be added into the bioreactor by any suitable means.

The bioreactor described herein is useful in the production of a biological product from a culture medium of a predetermined volume. In a related embodiment, the invention provides a method which contemplates providing a bioreactor as herein described, filling each container with an amount of culture medium sufficient to fill at least 50 vol. % of the internal volume of the container; activating the selectively movable base to impart motion to the culture medium; activating the recycle pump to recycle culture medium from the last container to the first container, the culture medium continuously flowing from the first container, to an intermediate container if present, and to the last container, during operation of the bioreactor; detecting the density of cells in the culture medium in a container at predetermined time intervals; and removing the culture medium and the biological product produced thereby from the bioreactor when the density of the cells in the culture medium in the container reaches a predetermined value.

The aforementioned apparatus and method permit the compositions of the culture media in each container to be maintained substantially constant relative to each other during operation of the bioreactor. This provides scalability to the production of a particular biological product, which is particularly desirable when a certain container (e.g., a container of a certain volume, composition and modifications (sensors, inlets, outlets, etc.)) has been validated for production, yet a quantity of biological product is desired which exceeds that which can be obtained from a single batch in that validated container. The use of the present invention, which employs an apparatus comprising inter alia a plurality of pre-validated (and, preferably, pre-sterilized) containers configured in unique and particular manner, allows one to vary the size of a biological production batch without the need for re-validation of the apparatus.

The composition of the culture medium is substantially constant when a first portion of culture medium in one container contains substantially the same concentration of components as a second portion of culture medium taken from a different container. Substantially the same concentration means a difference of no more than about 10%, desirably no more than about 5%, and more desirably no more than about 2%, depending on the composition of the culture medium.

It is also desirable that the containers do not include a mechanical mixing device, such as an impeller or paddle, within the container, or more desirably in any portion of the bioreactor. The present invention has been found to provide adequate mixing of the culture medium therein even in the absence of such mechanical mixing devices.

The foregoing relates to another aspect of the invention, this aspect providing a method of preparing a biological product in a bioreactor from a predetermined volume of culture medium. This method comprises the steps of: (a) determining the total amount of culture medium necessary to produce the desired amount of biological product; (b) selecting a plurality of containers of approximately equal internal volume, the plurality of containers comprising a first container, a last container and, optionally, one or more containers intermediate the first and last containers, wherein the quantity and internal volume of the selected containers allow the amount of culture medium in each container to exceed 50 vol. % of the container internal volume during operation of the bioreactor, with each of the containers being described in connection with the apparatus for preparing a biological product described herein. After this selection process is completed, (c) the bioreactor is assembled from the plurality of containers by (i) attaching a flow conduit to the at least one culture medium outlet of a container and into a subsequent container through the at least one culture medium inlet thereof to permit the flow of culture medium from the container into the subsequent container; (ii) attaching a recycle conduit which permits the flow of culture medium from the culture medium outlet of the last container and into the first container through the culture medium inlet thereof, (iii) incorporating a controllable pump into the recycle conduit to permit movement of the culture medium through the recycle conduit; and (iv) optionally, incorporating a valve for assisting in controlling the amount of culture medium which is recycled from the last container into the first container; (d) providing a base on which each container resides, wherein the base selectively imparts movement of the culture medium within each container during operation of the bioreactor; (e) introducing into each container an amount of culture medium sufficient to fill at least 50 vol. % of the internal volume of the container; (f) activating the selectively movable base to impart motion to the culture medium; (g) activating the controllable pump to recycle culture medium from the last container to the first container, the culture medium continuously flowing from the first container, to an intermediate container if present, and to the last container; (h) detecting the density of cells in the culture medium in a container at predetermined time intervals; and (i) removing the culture medium and the biological product produced thereby from the bioreactor when the density of the cells in the culture medium detected in the container reaches a predetermined value. In this method, the culture medium is continuously cycled through the containers which comprise the bioreactor during its operation, with the amount of culture medium that is recycled being variable, typically between 5 vol. % and 100 vol. %, the volume percent being calculated on the basis of the amount of culture medium in the final (last) container.

One of the advantages of the inventive bioreactor and related method is the increase in product yield per container volume that may be obtained relative to known systems. Contributing to this increase in yield is the capability of the bioreactor to operate when the amount of culture medium in each container exceeds 50 vol. %, based on the interior volume of the containers. Desirably, the amount of culture medium in each container during operation of the bioreactor may exceed about 60 vol. % of the interior volume of the container, more desirably it may exceed about 70 vol. %, even more desirably it may exceed about 80 vol. %, it may preferably exceed about 85 vol. %, and more preferably it may exceed about 90 vol. % thereof. This increase in culture medium volume on a percentage basis not only provides relatively high yields per volume, but may be achieved even if the culture medium initially introduced into the bioreactor, or as present in the bioreactor during and/or after processing, contains relatively low levels of anti-foaming agents such as Antifoam 2210 or Compound A (Dow Corning), M-10 (Calgene), Breox FMT 30 International Specialty Company), or A6582, A6457, A6707, A8082 and A8582 (Sigma Aldrich) (from about 0.001 wt. % to about 0.005 wt. %). More desirably, the culture medium initially introduced into the bioreactor, or as present in the bioreactor during and/or after processing, is substantially free of such anti-foaming agents (from about 0.0001 wt. % to about 0.001 wt. %, or less than about 0.001 wt %).

The operation of the bioreactor with the aforementioned volumes may be attributed in part to the use of a foam trap. The foam trap, which is in fluid communication with the gas outlet of a container, is able to process the foam produced in the container during operation of the bioreactor into liquid, and return the liquid to the container. A foam trap useful in the various aspects of the invention comprises a chamber, desirably a flexible chamber, the chamber comprising an inlet in fluid communication with the gas outlet of a container to permit any foam present in the container to enter the chamber, a gas outlet, and an outlet in fluid communication with the foam trap inlet of the container, each container further comprising a tubular member in fluid communication with the foam trap inlet, the tubular member having an opening which is submerged in the culture medium of the container during operation of the bioreactor, a selectively-operable antifoam agent dispersing device, which, when activated, disperses antifoam agent of a type and quantity sufficient to cause the foam present in the chamber to collapse into a liquid, wherein liquid present in the chamber exits the chamber outlet and enters the culture medium of the container by passing through the tubular member, and a foam sensor which detects the presence of foam in the chamber, wherein the foam sensor sends a first signal to the antifoam dispersing device causing the device to disperse antifoam agent when foam is detected in the chamber, and a second signal to the antifoam dispersing device causing the device to cease dispersion of the antifoam agent when foam is absent from the chamber.

Figure 7A:
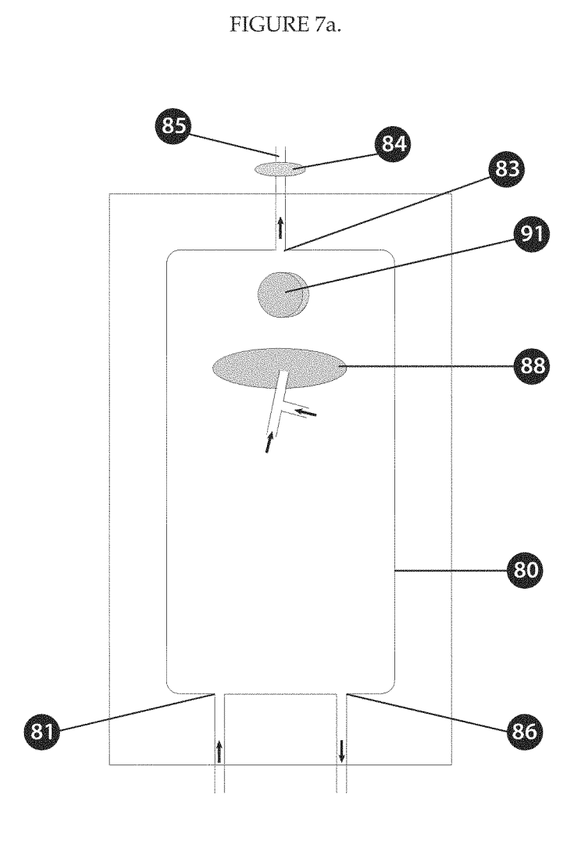
FIGS. 7a and 7b are side sectional views of a bioreactor foam trap in accordance with another preferred embodiment of the invention.
Figure 7B:
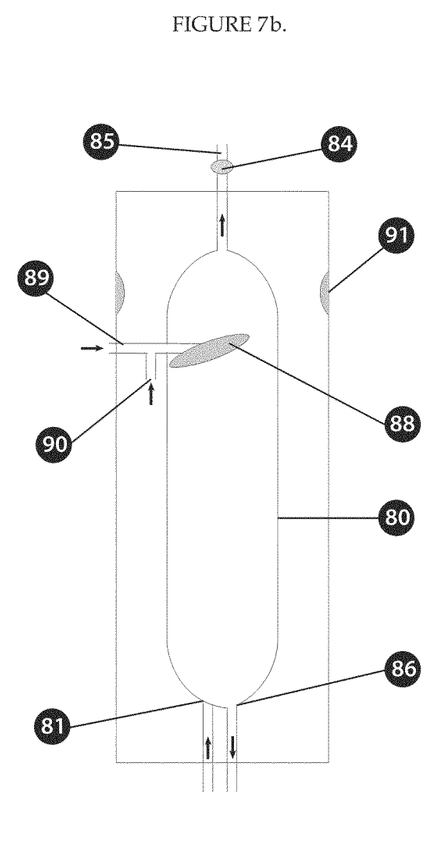

Turning to FIGS. 7a and 7b, there are illustrated two side (sectional) views of a preferred foam trap useful in the various aspects of the invention described herein. These views are of a section of the device when viewed from the front, and a view after the device is rotated 90 degrees. In this embodiment, the foam trap comprises a chamber 80. The chamber comprises an inlet 81 which is in fluid communication with the gas outlet of a container 37. Desirably, a foam trap conduit 82 provides for this fluid communication. This arrangement permits an amount of foam which exceeds the headspace volume of a container (this foam being generated during operation of the bioreactor) to pass out of the container through the gas outlet 37 and into the foam trap chamber 80. The chamber 80 also includes a gas outlet 83, the latter optionally comprising a submicron air filter 84 (desirably 0.22 microns) and a vent 85 to assist in ensuring that the interior of the foam trap, and ultimately the entire apparatus of which the foam trap is part, remains at the desired pressure, and also sterile. An outlet 86 in the chamber is also provided, this outlet being in fluid communication with the foam trap inlet 39 of the container via a hollow member 87 (desirably a flexible, sterilizable tube) through which the liquid in the chamber (i.e., foam that has been subjected to processing in the chamber) may flow from the foam trap and into a container. This hollow member should have at least one opening at the end which is submerged in the culture medium residing in a container so that the liquid provided upon operation of the foam trap enters the liquid culture medium. It should be appreciated that one foam trap may be in fluid communication with more than one container.

The processing of the foam into liquid within the chamber may be accomplished by the use of an antifoam dispersion device. In the embodiment illustrated in FIGS. 7a and 7b, this dispersion device is controllable and, when activated, produces a fine mist of the antifoam agent within the chamber in an amount sufficient to convert foam therein into liquid. Desirably, the dispersion device further provides for application of the antifoam agent to the foam via contact, sometimes referred to as wicking. The device illustrated in FIGS. 7a and 7b is able disperse antifoam agent via both misting and wicking. This device preferably comprises a disk-type sparger 88 inside the chamber 80, the former more preferably being located in the upper half of the chamber 80. The sparger is in fluid communication with a source of antifoam agent 90 and a controllable air supply 89. When foam is detected in the chamber, the air supply is activated, and begins to move air and antifoam agent (which has also been released) through the sparger, thereby providing a mist within the chamber which contacts the foam and converts a relatively large amount of foam present in the chamber (e.g., more than about 50 vol. %, more desirably more than about 70 vol. %, and most desirably more than about 90 vol. %) into liquid. In a related embodiment, the antifoam agent is slowly and continuously released through the sparger in the absence of air to collapse the foam as it comes in contact with the sparger.

The sparger desirably comprises porous ceramic diffusers, which are commonly referred to as wicks or applicators. These materials permit precise control over porosity and pore size. These porous ceramics are manufactured by fusing aluminum oxide grains using a porcelain bond which provides a strong, uniformly porous and homogeneous structure capable of producing fine bubbles. Desirably, the porous ceramic may have 40-50% open porosity, and a pore size ranging from about 0.25 to about 90 microns (e.g., aluminum oxide porous ceramic is available in 6, 15, 30, 50, 60 and 90 micron pore sizes; a ceramic membrane comprising a medium pore substrate with a thin coating of fine porous ceramic membrane is available in 0.25, 1, 3 and 6 micron pore sizes). The aforesaid ceramics may be of any suitable size, including but not limited to tubes (from ½" to 4" diameter), discs (from 1" to 9" diameter) and plates (up to 12" square). Suitable porous ceramic diffusers are available from Refractron Technologies Corp., Newark, N.Y.).

Detection of the foam is desirably provided by a thermal or photo sensor 91 is also provided as part of the foam trap which detects the presence of foam in the flexible chamber. When foam is detected, this sensor sends a first signal to the antifoam device activating the device and causing it to emit antifoam agent into the chamber, and after such activation, when foam is no longer detected in the chamber, the sensor sends a second signal to the antifoam device causing the device to cease emitting antifoam agent into the chamber.

In a related aspect, the invention thus provides a method for producing a biological product from a culture medium of a predetermined volume comprising (a) providing a bioreactor as described herein; (b) filling each container with an amount of culture medium sufficient to fill at least 50 vol. % of the internal volume of the container; (c) activating the selectively movable base to impart motion to the culture medium; (d) activating the pump to recycle culture medium from the last container to the first container, the culture medium continuously flowing from the first container, to an intermediate container if present, and to the last container; (e) detecting the presence of foam in the chamber of the foam trap and, if foam is present, activating an antifoam agent dispersion device which converts foam into a liquid, the antifoam agent being dispersed on a continuous or intermittent basis; (e) detecting the density of cells in the culture medium in a container at predetermined time intervals; and (f) removing the culture medium and the biological product produced thereby from the bioreactor when the density of the cells in the culture medium reaches a predetermined value.

Turning to FIG. 1, the sparging filter (or sparger) 36 used to efficiently introduce an oxygenated gas into the container 30 includes a plurality of pores therein, wherein at least one of the pores, and more desirably all of the pores, of the sparging filter are immersed in the culture medium during operation of the bioreactor. Desirably, the sparging filter is located at the bottom of the container, adjacent the bottom wall thereof. This arrangement has been found to maximize the oxygenation of the culture medium (the mixing thereof), as the gas bubbles move upward relative to the culture medium which, upon operation of the bioreactor, moves downward and out of the container through the culture medium outlet, the latter desirably being located in the bottom of the container. When relatively delicate mammalian cells are present in the culture medium, this imparts less turbulence to the culture medium yet allows less oxygen to be introduced because the oxygenation of the culture medium is more efficient. The relatively lower amount of gas introduced (relative to known processes) has the further advantage of generating less foam in the headspace of the container.

Preferably, the size of each immersed pore does not exceed 50 µm, as it has been found that the bubbles generated in the culture medium when gas is introduced therein via the sparger should be relatively small in size as certain cells may be damaged by relatively large bubbles. It is thus preferred that the average size of the bubbles generated by the sparger does not exceed about 500 µm.

The sparging filter may be provided in any suitable size or shape, and a plurality of such filters may be provided in each container. Desirably, the sparger may comprise a hollow tubular structure having a length ranging from about ¼ to about ¾ of longest dimension of the container as measured while the container resides on the base (this taking into account the different size containers that may successfully be used in the invention). In this configuration, the pores are desirably located along the length of the sparger to more efficiently distribute the oxygenated gas emitted therefrom throughout the culture medium, the latter having a closed end, and wherein more desirably the size of the pores increases along the length of the filter and are largest nearest the closed end. This arrangement compensates for the loss in gas pressure from the sparger inlet to the closed end, providing for the bubbles generated by the sparger to have a relatively constant size along the length of the sparger. In this regard, it is further preferred that the size of the largest pore in the sparger is between about 40% and about 70% larger relative to the size of the smallest pore.

Sparging may be run continuously, periodically, or in some cases, in response to certain events, e.g., within a bioreactor system and/or within an individual container. For example, the spargers may be connected to one or more sensors and a control system which is able to monitor the amount of sparging, the degree of foaming, the amount or concentration of a substance in the container, and respond by initiating, reducing, or increasing the degree of sparging of one or more compositions of gases.

Each container is provided with a gas outlet which includes a pressure valve and submicron filter, the former assisting in maintaining the pressure within the container at a desired range while the latter assists in maintaining sterility of the culture medium. Desirably, the pressure in the container is maintained at ambient conditions, preferably ranging from about to about 0.1 to 1 psig. The filter may be of any suitable size and porosity, but is preferably a HEPA filter, having an average porosity of from about 0.3 µm to about 0.1 µm, and more preferably of about 0.22 µm.

In a further embodiment of the invention, there is provided a method which permits the continuous preparation of biological products. This method comprises (a) providing a bioreactor system comprising (i) a plurality of containers for retaining the culture medium, the plurality of containers comprising a first container, a last container and a container intermediate the first and last containers, each container comprising at least one culture medium inlet, at least one culture medium outlet, at least one gas inlet, at least one sparging filter attached to the at least one gas inlet, the filter comprising a plurality of pores on at least a portion thereof, the portion of the filter comprising the pores extending into the culture medium, at least one gas exhaust, at least one foam trap attached to the at least one gas exhaust, at least one inlet in fluid communication with the foam trap, one or more sensors for sensing one or more parameters of the culture medium, (ii) a flow conduit comprising a valve which permits the flow of culture medium through the at least one culture medium outlet of a container and into a subsequent container through the at least one culture medium inlet thereof, (iii) at least one selectively movable base which supports each container, wherein movement of the base induces movement of the culture medium within each container, (b) charging the first container with culture medium, (c) moving the culture medium in the first container while introducing oxygen into the medium through the sparging filter until the desired density of the cells in the culture medium is obtained, (d) opening the valve in the flow conduit located between the first container and the intermediate container to permit the culture medium from the first container to enter the intermediate container, and closing the valve thereafter, (e) charging the first container with a culture medium comprising the component included in the culture medium of step (b), and adding culture medium to the cell culture medium present in the intermediate container, (f) moving the culture medium in each container while introducing oxygen into the medium through the sparging filter until the desired density of the cells in the culture medium in each container is obtained, (g) opening the valve in the flow conduit located between an intermediate container and the last container to permit the culture medium from the intermediate container to enter the last container, and closing the valve thereafter, (h) charging the first container with a culture medium comprising the component included in the culture medium of step (b), and adding culture medium to the culture medium present in each intermediate and last containers, (i) moving the culture medium in each container while introducing oxygen into each medium through the sparging filter until the desired density of the cells in the culture medium in each container is obtained, (j) removing the culture medium from the last container, opening the valve in the flow conduit located between an intermediate container and the last container to permit the culture medium from the intermediate container to enter the last container and closing the valve thereafter, and opening the valve in the flow conduit located between the first container and the subsequent intermediate container to permit the culture medium from the first container to enter the subsequent intermediate container and closing the valve thereafter, (k) charging the first container with a culture medium and, optionally, with the component included in the culture medium of step (b), and adding culture medium to the culture medium present in each of the intermediate and last containers, (l) moving the culture medium in each container while introducing oxygen into the culture medium through the sparging filter until the desired density of the cells in the culture medium in each container is obtained, and (m) repeating steps (j)-(l). Desirably, cell culture is charged into the first container during step (k).

Figure 6:
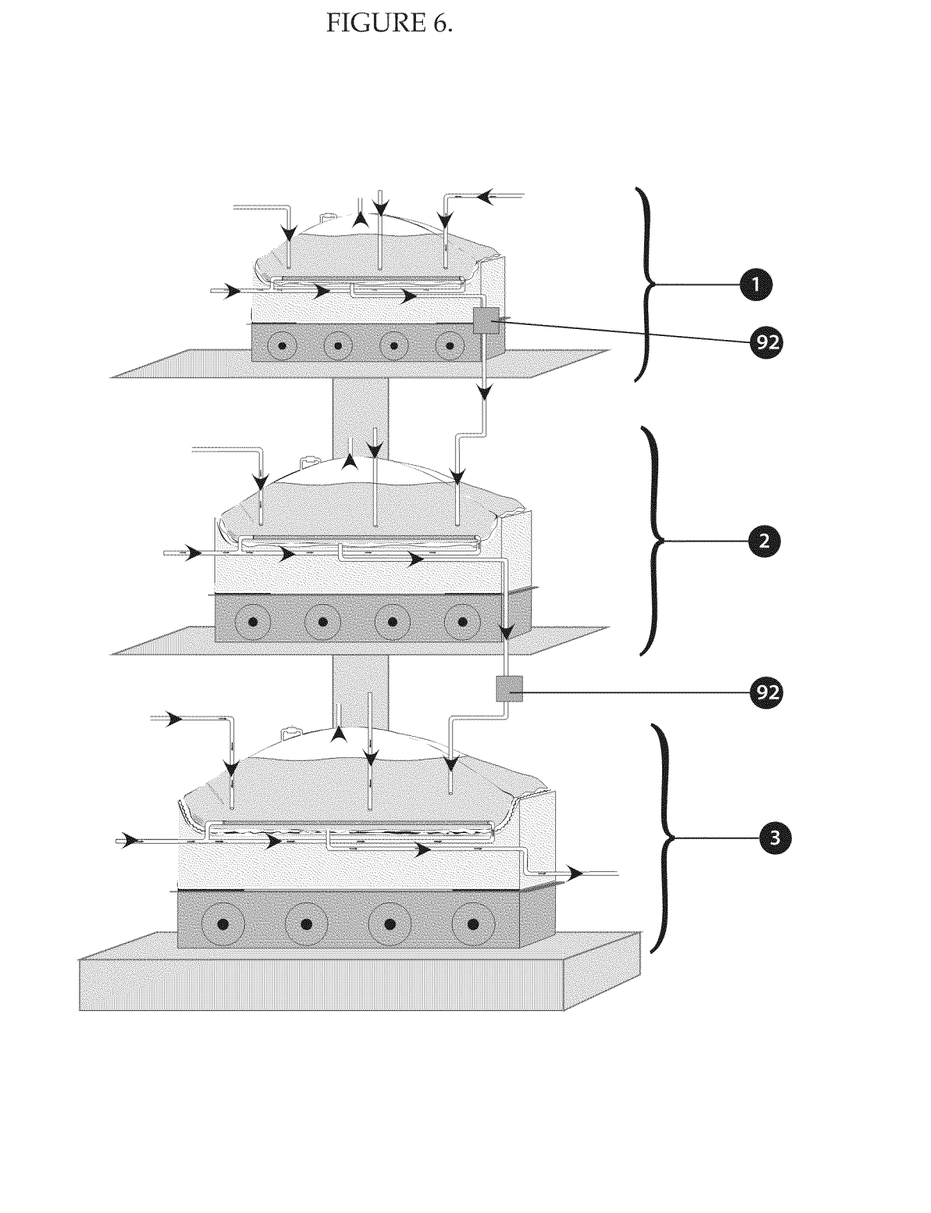
FIG. 6 is an illustration of a bioreactor in accordance with another preferred embodiment of the invention.

Turning to FIG. 6, there is provided an illustration of an apparatus that may be used to practice the aforementioned inventive method. The containers 1, 2 3 and movable bases associated therewith, shown in a sectional view, desirably have the properties and features of those devices described in connection with the bioreactor described herein, and thus a description of same will not be repeated. This being said, certain additional features associated with this embodiment of the invention will be described in the following paragraphs.

In this method, and as shown in FIG. 6, it is desired that each container is associated with a selectively movable base which supports that container, and that the movement of each base is independently controllable so that the movement of culture medium in the first, intermediate and last containers may differ relative to each other. This allows one to tailor the extent of mixing of the culture medium in each container according to the particular composition of the culture medium therein.

It is further desirable that each container be located within a climate-controlled environment. More desirably, the containers and corresponding movable bases reside within a chamber which permits independent control of one or more of the temperature of the ambient air within the enclosure, of the air quality, and of the radiation to which the containers are exposed. Preferably, the environment permits the independent control of the ambient temperature, air quality and radiation for each container independently of the other containers.

Preferably, and as illustrated in FIG. 6, the first 1, intermediate 2 and last 3containers are arranged in a sequential vertical orientation, wherein the first container is positioned higher relative to the intermediate and last containers, and each intermediate container is positioned higher relative to the last container. This reduces (or perhaps eliminates) the need for mechanical assistance in transferring the culture medium between containers, as gravitation force should be able to complete the transfer. This embodiment desirably includes a plurality of controllable pumps 92 which assist in the transfer of culture medium from one container to another container.

While the internal volume of the containers may vary, it is desirable that the internal volume of the intermediate container ranges from about 2 to about 20 times the internal volume of the first container, and the internal volume of the last container range from about 5 to about 20 times the internal volume of the intermediate container. More desirably, the internal volume of the intermediate container ranges from about 5 to about 15 times the internal volume of the first container, and the internal volume of the last container range from about 5 to about 15 times the internal volume of the intermediate container.

Generally, the invention provides bioreactors and methods which are universal in the sense that the invention is suitable and adaptable for processing a variety of compositions, including both biologic and non-biologic components. Indeed, an inventive bioreactor designed for use with mammalian cells, for example, may be used for culturing bacteria, allowing ease of manufacturing.

As used herein, the term "culture medium" is intended to encompass compositions which include biologic components as described herein.

Compositions comprising non-biologic components include, but are not limited to, those which comprise microcarriers (e.g., polymer spheres, solid spheres, gelatinous particles, microbeads, and microdisks that can be porous or non-porous), cross-linked beads (e.g., dextran) charged with specific chemical groups (e.g., tertiary amine groups), 2D microcarriers including cells trapped in nonporous polymer fibers, 3D carriers (e.g., carrier fibers, hollow fibers, multi-cartridge reactors, and semi-permeable membranes that can comprising porous fibers), microcarriers having reduced ion exchange capacity, cells, capillaries, and aggregates (e.g., aggregates of cells).

The biological components that may be processed in accordance with the invention are described in the paragraphs which follow and include, but are not limited to, cell cultures derived from sources such as animals (e.g., hamsters, mice, pigs, rabbits, dogs, fish, shrimp, nematodes, and humans), insects (e.g., moths and butterflies), plants (e.g., algae, corn, tomato, rice, wheat, barley, alfalfa, sugarcane, soybean, potato, lettuce, lupine, tobacco, rapeseed (canola), sunflower, turnip, beet cane molasses, seeds, safflower, and peanuts), bacteria, fungi, and yeast.

Illustrative animal cells include Chinese hamster ovary (CHO), mouse myeloma, M0035 (NSO cell line), hybridomas (e.g., B-lymphocyte cells fused with myeloma tumor cells), baby hamster kidney (BHK), monkey COS, African green monkey kidney epithelial (VERO), mouse embryo fibroblasts (NIH-3T3), mouse connective tissue fibroblasts (L929), bovine aorta endothelial (BAE-1), mouse myeloma lymphoblastoid-like (NSO), mouse B-cell lymphoma lymphoblastoid (WEHI 231), mouse lymphoma lymphoblastoid (YAC 1), mouse fibroblast (LS), hepatic mouse (e.g., MC/9, NCTC clone 1469), and hepatic rat cells (e.g., ARL-6, BRL3A, H4S, Phi 1 (from Fu5 cells)).

Illustrative human cells include retinal cells (PER-C6), embryonic kidney cells (HEK-293), lung fibroblasts (MRC-5), cervix epithelial cells (HELA), diploid fibroblasts (WI38), kidney epithelial cells (HEK 293), liver epithelial cells (HEPG2), lymphoma lymphoblastoid cells (Namalwa), leukemia lymphoblastoid-like cells (HL60), myeloma lymphoblastoid cells (U 266B1), neuroblastoma neuroblasts (SH-SY5Y), diploid cell strain cells (e.g., propagation of poliomyelitis virus), pancreatic islet cells, embryonic stem cells (hES), human mesenchymal stem cells (MSCs, which can be differentiated to osteogenic, chondrogenic, tenogenic, myogenic, adipogenic, and marrow stromal lineages, for example), human neural stem cells (NSC), human histiocytic lymphoma lymphoblastoid cells (U937), and human hepatic cells such as WRL68 (from embryo cells), PLC/PRF/5 (i.e., containing hepatitis B sequences), Hep3B (i.e., producing plasma proteins: fibrinogen, alpha-fetoprotein, transferrin, albumin, complement C3 and/or alpha-2-macroglobulin), and HepG2 (i.e., producing plasma proteins: prothrombin, antithrombin III, alpha-fetoprotein, complement C3, and/or fibrinogen).

Cells from insects (e.g., baculovirus and *Spodoptera frugiperda* ovary (Sf21 cells produce Sf9 line)) and cells from plants or food, may also be cultured in accordance with the invention. Cells from sources such as rice (e.g., *Oryza sativa, Oryza sativa* cv Bengal callus culture, and *Oryza sativa* cv Taipei 309), soybean (e.g., *Glycine max* cv Williams 82), tomato (*Lycopersicum esculentum* cv Seokwang), and tobacco leaves (e.g., *Agrobacterium tumefaciens* including Bright Yellow 2 (BY-2), *Nicotiana tabacum* cv NT-1, *N. tabacum* cv BY-2, and *N. tabacum* cv Petite Havana SR-1) are illustrative examples.

Bacteria, fungi, or yeast may also be cultured in accordance with the invention. Illustrative bacteria include *Salmonella, Escherichia coli, Vibrio cholerae, Bacillus subtilis, Streptomyces, Pseudomonas fluorescens, Pseudomonas putida, Pseudomonas* sp, *Rhodococcus* sp, *Streptomyces* sp, and *Alcaligenes* sp. Fungal cells can be cultured from species such as *Aspergillus niger* and *Trichoderma reesei*, and yeast cells can include cells from *Hansenula polymorpha, Pichia pastoris, Saccharomyces cerevisiae, S. cerevisiae* crossed with *S. bayanus, S. cerevisiae* crossed with LAC4 and LAC1-2 genes from *K. lactis, S. cerevisiae* crossed with *Aspergillus shirousamii, Bacillus subtilis, Saccharomyces diastasicus, Schwanniomyces occidentalis, S. cerevisiae* with genes from *Pichia stipitis*, and *Schizosaccharomyces pombe*.

A variety of different products may also be produced in accordance with the invention. Illustrative products include proteins (e.g., antibodies and enzymes), vaccines, viral products, hormones, immunoregulators, metabolites, fatty acids, vitamins, drugs, antibiotics, cells, and tissues. Non-limiting examples of proteins include human tissue plasminogen activators (tPA), blood coagulation factors, growth factors (e.g., cytokines, including interferons and chemokines), adhesion molecules, Bcl-2 family of proteins, polyhedrin proteins, human serum albumin, scFv antibody fragment, human erythropoietin, mouse monoclonal heavy chain 7, mouse $IgG_{2b/k}$, mouse IgG1, heavy chain mAb, Bryondin 1, human interleukin-2, human interleukin-4, ricin, human α1-antitrypisin, biscFv antibody fragment, immunoglobulins, human granulocyte, stimulating factor (hGM-CSF), hepatitis B surface antigen (HBsAg), human lysozyme, IL-12, and mAb against HBsAg. Examples of plasma proteins include fibrinogen, alpha-fetoprotein, transferrin, albumin, complement C3 and alpha-2-macroglobulin, prothrombin, antithrombin III, alpha-fetoprotein, complement C3 and fibrinogen, insulin, hepatitis B surface antigen, urate oxidase, glucagon, granulocyte-macrophage colony stimulating factor, hirudin/desirudin, angiostatin, elastase inhibitor, endostatin, epidermal growth factor analog, insulin-like growth factor-1, kallikrein inhibitor, α1-antitrypsin, tumor necrosis factor, collagen protein domains (but not whole collagen glycoproteins), proteins without metabolic byproducts, human albumin, bovine albumin, thrombomodulin, transferrin, factor VIII for hemophilia A (i.e., from CHO or BHK cells), factor VIIa (i.e., from BHK), factor IX for hemophilia B (i.e., from CHO), human-secreted alkaline phosphatase, aprotinin, histamine, leukotrienes, IgE receptors, N-acetylglucosaminyltransferase-III, and antihemophilic factor VIII.

Enzymes may be produced from a variety of sources using the invention. Non-limiting examples of such enzymes include YepACT-AMY-ACT-X24 hybrid enzyme from yeast, *Aspergillus oryzae* α-amylase, xylanases, urokinase, tissue plasminogen activator (rt-PA), bovine chymosin, glucocerebrosidase (therapeutic enzyme for Gaucher's disease, from CHO), lactase, trypsin, aprotinin, human lactoferrin, lysozyme, and oleosines.

Vaccines also may be produced using the invention. Non-limiting examples include vaccines for prostate cancer, human papilloma virus, viral influenza, trivalent hemagglutinin influenza, AIDS, HIV, malaria, anthrax, bacterial meningitis, chicken pox, cholera, diphtheria, *haemophilus influenza* type B, hepatitis A, hepatitis B, pertussis, plague, pneumococcal pneumonia, polio, rabies, human-rabies, tetanus, typhoid fever, yellow fever, veterinary-FMD, New Castle's Disease, foot and mouth disease, DNA, Venezuelan equine encephalitis virus, cancer (colon cancer) vaccines (i.e., prophylactic or therapeutic), MMR (measles, mumps, rubella), yellow fever, *Haemophilus influenzae* (Hib), DTP (diphtheria and tetanus vaccines, with pertussis subunit), vaccines linked to polysaccharides (e.g., Hib, *Neisseria meningococcus*), *Staphylococcus pneumoniae*, nicotine, multiple sclerosis, bovine spongiform encephalopathy (mad cow disease), IgG1 (phosphonate ester), IgM (neuropeptide hapten), SIgA/G (*Streptococcus mutans* adhesin), scFv-bryodin 1 immunotoxin (CD-40), IgG (HSV), LSC(HSV), Norwalk virus, human cytomegalovirus, rotavirus, respiratory syncytial virus F, insulin-dependent autoimmune mellitus diabetes, diarrhea, rhinovirus, herpes simplex virus, and personalized cancer vaccines, e.g., for lymphoma treatment (i.e., in injectable, oral, or edible forms). Recombinant subunit vaccines also may be produced, such as hepatitis B virus envelope protein, rabies virus glycoprotein, *E. coli* heat labile enterotoxin, Norwalk virus capsid protein, diabetes autoantigen, cholera toxin B subunit, cholera toxin B an dA2 subunits, rotavirus enterotoxin and enterotoxigenic *E. coli*, fimbrial antigen fusion, and porcine transmissible gastroenteritis virus glycoprotein S.

Viral products also may be produced. Non-limiting examples of viral products include sindbis, VSV, oncoma, hepatitis A, channel cat fish virus, RSV, corona virus, FMDV, rabies, polio, reo virus, measles, and mumps.

Hormones also may be produced using the invention. Non-limiting examples of hormones include growth hormone (e.g., human growth hormone (hGH) and bovine growth hormone), growth factors, beta and gamma interferon, vascular endothelial growth factor (VEGF), somatostatin, platelet-derived growth factor (PDGF), follicle stimulating hormone (FSH), luteinizing hormone, human chorionic hormone, and erythropoietin.

Immunoregulators also may be produced. Non-limiting examples of immunoregulators include interferons (e.g., beta-interferon (for multiple sclerosis), alpha-interferon, and gamma-interferon) and interleukins (such as IL-2).

Metabolites (e.g., shikonin and paclitaxel) and fatty acids (i.e., including straight-chain (e.g., adipic acid, Azelaic acid, 2-hydroxy acids), branched-chain (e.g., 10-methyl octadecanoic acid and retinoic acid), ring-including fatty acids (e.g., coronaric acid and lipoic acid), and complex fatty acids (e.g., fatty acyl-CoA)) also may be produced.

The containers useful in the various embodiments of the invention may be of any size suitable for containing a liquid. For example, the container may have a volume between 1-40 L, 40-100 L, 100-200 L, 200-300 L, 300-500 L, 500-750 L, 750-1,000 L, 1,000-2,000 L, 2,000-5,000 L, or 5,000-10,000 L. In some instances, the container has a volume greater than 1 L, or in other instances, greater than 10 L, 20 L, 40 L, 100 L, 200 L, 500 L, or 1,000 L. Volumes greater than 10,000 L are also possible, but not desirable. Preferably, the container volume will range between about 1 L and 1000 L, and more preferably between about 5 L and 500 L, and even more preferably between 5 L and 200 L.

The components of the bioreactors and other devices described herein which come into contact with the culture medium or products provided thereby desirably comprise biocompatible materials, more desirably biocompatible polymers, and are preferably sterilizable.

It should also be understood that many of the components described herein also are desirably flexible, e.g., the containers and foam trap chambers desirably comprise flexible biocompatible polymer containers (such as collapsible bags), with the conduits also desirably comprising such biocompatible polymers. The flexible material is further desirably one that is USP Class VI certified, e.g., silicone, polycarbonate, polyethylene, and polypropylene. Non-limiting examples of flexible materials include polymers such as polyethylene (e.g., linear low density polyethylene and ultra low density polyethylene), polypropylene, polyvinylchloride, polyvinyldichloride, polyvinylidene chloride, ethylene vinyl acetate, polycarbonate, polymethacrylate, polyvinyl alcohol, nylon, silicone rubber, other synthetic rubbers and/or plastics. If desired, portions of the flexible container may comprise a substantially rigid material such as a rigid polymer (e.g., high density polyethylene), metal, and/or glass.

Desirably the containers comprise biocompatible materials, more desirably biocompatible polymers. When collapsible containers are selected for use, the container may be supported by or may line an inner surface of a support structure, e.g., the base platform, the latter having container-retaining sidewalls. However, the invention may be practiced using non-collapsible or rigid containers or conduits.

The containers (or foam trap chamber) may have any thickness suitable for retaining the culture medium therewithin, and may be designed to have a certain resistance to puncturing during operation or while being handled. For example, the walls of a container may have a total thickness of less than or equal to 250 mils (1 mil is 25.4 micrometers), less than or equal to 200 mils, less than or equal to 100 mils, less than or equal to 70 mils (1 mil is 25.4 micrometers), less than or equal to 50 mils, less than or equal to 25 mils, less than or equal to 15 mils, or less than or equal to 10 mils. In certain embodiments, the container may include more than one layer of material that may be laminated together or otherwise attached to one another to impart certain properties to the container. For instance, one layer may be formed of a material that is substantially oxygen impermeable. Another layer may be formed of a material to impart strength to the container. Yet another layer may be included to impart chemical resistance to fluid that may be contained in the container.

It thus should be understood that a container may be formed of any suitable combinations of layers. The container (e.g., collapsible bag) may include, for example, 1 layer, greater than or equal to 2 layers, greater than or equal to 3 layers, or greater than or equal to 5 layers of material(s). Each layer may have a thickness of, for example, less than or equal to 200 mils, less than or equal to 100 mils, less than or equal to 50 mils, less than or equal to 25 mils, less than or equal to 15 mils, less than or equal to 10 mils, less than or equal to 5 mils, or less than or equal to 3 mils, or combinations thereof.

In addition, the container preferably is seamless in order to improve its strength and avoid deposition of growing cells in the media.

All or portions of the container also are desirably translucent, or more desirably transparent, to allow viewing of contents inside the container. The latter is preferred when it is desirable to irradiate the culture medium within the container.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

I claim:

1. A method for the continuous preparation of a biological product from a culture medium comprising:
　(a) providing a bioreactor system comprising:
　　(i) a plurality of vertically disposed disposable containers for retaining the culture medium, the plurality of containers comprising a first disposable container disposed at the highest level, a last disposable container disposed at the lowest level and an intermediate disposable container disposed intermediate to the first and last containers, each container comprising:
　　at least one culture medium inlet,
　　at least one culture medium outlet separate from the at least one culture medium inlet, wherein fluid can flow out of the at least one culture medium outlet at the same time that fluid flows into the at least one culture medium inlet,
　　at least one gas inlet,
　　at least one sparging filter attached to the at least one gas inlet, the sparging filter comprising a plurality of pores on at least a portion thereof, the portion of the filter comprising the pores extending into the culture medium,
　　at least one gas exhaust, at least one foam trap attached to the at least one gas exhaust, at least one inlet in fluid communication with the foam trap, one or more sensors for sensing one or more parameters of the culture medium, (ii) a flow conduit comprising a valve which permits the flow of culture medium under gravity through the at least one culture medium outlet of a container and into a subsequent container through the at least one culture medium inlet thereof, (iii) at least one selectively movable base which supports each container, wherein movement of the base induces movement of the culture medium within each container, (b) charging the first container with culture medium comprising a component selected from the group consisting of mammalian cells, plant cells and bacteria, (c) moving the culture medium in the first container while introducing oxygen into the medium through the sparging filter until the desired density of the cells in the culture medium is obtained, (d) opening the valve in the flow conduit located between the first container and the intermediate container to permit the culture medium from the first container to enter the intermediate container continuously at a pre-determined rate, (e) charging continuously the first container with a culture medium comprising the component included in the culture medium of step b to make up the volume of the culture medium transferred to the intermediate container, and continue moving the culture medium in the first container, and adding culture medium to the cell culture medium present in the intermediate container to a pre-determined volume, (f) continuously moving the culture medium in intermediate container while introducing oxygen into the medium through the sparging filter until the desired density of the cells in the culture medium of the intermediate container is obtained, (g) opening the valve in the flow conduit located between an intermediate container and the last container to permit the culture medium from the intermediate container to enter the last container, continuously at a pre-determined rate, (h) charging continuously the intermediate container with a culture medium to replace the volume transferred to the last container, and adding culture medium to the culture medium present in the last container to a pre-determined volume, (i) moving the culture medium in the last container while introducing oxygen into each medium through the sparging filter until the desired density of the cells in the culture medium in the last container is obtained, (j) removing the culture medium continuously from the last container by opening the valve in the flow conduit in last container and collecting the culture medium in a receptacle for further processing, and continuously adding culture medium to the culture medium present in the last container to maintain the pre-determined volume of the culture medium in the last container.

\* \* \* \* \*